United States Patent
Mariani

(10) Patent No.: US 12,208,198 B2
(45) Date of Patent: Jan. 28, 2025

(54) INHALER AND METHOD

(71) Applicant: Nick Mariani, Coconut Creek, FL (US)

(72) Inventor: Nick Mariani, Coconut Creek, FL (US)

( * ) Notice: Subject to any disclaimer, the term of this patent is extended or adjusted under 35 U.S.C. 154(b) by 902 days.

(21) Appl. No.: 16/981,944

(22) PCT Filed: Mar. 29, 2019

(86) PCT No.: PCT/US2019/024902
§ 371 (c)(1),
(2) Date: Sep. 17, 2020

(87) PCT Pub. No.: WO2019/191628
PCT Pub. Date: Oct. 3, 2019

(65) Prior Publication Data
US 2021/0187212 A1  Jun. 24, 2021

Related U.S. Application Data

(60) Provisional application No. 62/650,464, filed on Mar. 30, 2018.

(51) Int. Cl.
*A61M 11/04* (2006.01)
*A61M 15/00* (2006.01)

(52) U.S. Cl.
CPC ........ *A61M 11/04* (2013.01); *A61M 15/0025* (2014.02); *A61M 15/0028* (2013.01)

(58) Field of Classification Search
CPC .............. A61M 11/04; A61M 15/0025; A61M 15/0028; A61M 15/06; A24F 42/20
See application file for complete search history.

(56) References Cited

U.S. PATENT DOCUMENTS

| | | | | |
|---|---|---|---|---|
| 346,909 A * | 8/1886 | Hamersly | ............. | A61M 15/00 128/203.23 |
| 844,097 A * | 2/1907 | Caldwell | ............... | A61M 15/08 128/203.22 |
| 928,884 A * | 7/1909 | Randall | .................. | A61M 15/06 128/203.24 |
| 1,410,556 A * | 3/1922 | Dorment | ............... | A61M 15/00 128/203.24 |
| 1,442,253 A * | 1/1923 | Daniel | .................. | A61M 15/00 128/203.22 |
| 1,870,558 A * | 8/1932 | Darby | ................... | A61M 15/08 128/203.21 |

(Continued)

FOREIGN PATENT DOCUMENTS

| | | | |
|---|---|---|---|
| CH | 656803 A5 | * | 7/1986 |
| LT | 3123 B | * | 12/1994 |

OTHER PUBLICATIONS

English translation for LT 3123, translated by Search Clarivate Analytics, translated on Jul. 13, 2023.*

(Continued)

*Primary Examiner* — Tu A Vo
(74) *Attorney, Agent, or Firm* — Ted Whitlock

(57) ABSTRACT

An apparatus for oral inhalation-driven administration of therapeutic substances to the airways and lungs of a human subject, which includes a body portion having one or more air intakes for the intake of ambient air, a mouthpiece, and a cartridge receiving port for receiving and engaging a dispensing cartridge containing at least one volatile therapeutic substance.

9 Claims, 3 Drawing Sheets

(56) References Cited

U.S. PATENT DOCUMENTS

| | | | | |
|---|---|---|---|---|
| 1,923,650 | A | * | 8/1933 | Westerfield ....... A61M 15/0025 128/203.24 |
| 2,191,016 | A | * | 2/1940 | Hoffman ............... A61M 15/08 128/203.23 |
| 3,565,071 | A | * | 2/1971 | Cobb .................... A61M 15/06 131/273 |
| 4,184,496 | A | * | 1/1980 | Adair ................ A61M 15/0008 131/271 |
| 4,576,157 | A | * | 3/1986 | Raghuprasad .... A61M 15/0093 128/200.23 |
| 2009/0151716 | A1 | * | 6/2009 | Abrams ............ A61M 15/0028 128/200.14 |
| 2016/0295919 | A1 | * | 10/2016 | Thomas, Jr. ......... A61M 11/042 |
| 2017/0368273 | A1 | * | 12/2017 | Rubin ............... A61M 16/0093 |
| 2018/0140789 | A1 | * | 5/2018 | Pieters ............. A61M 15/0021 |
| 2020/0086070 | A1 | * | 3/2020 | Kern ................ A61M 15/0085 |

OTHER PUBLICATIONS

Definition of the term "cartridge" from collinsdictionary.com, captured on Mar. 28, 2024.*

Definition of the term "cartridge" from Cambridge.org, cpatured on Mar. 28, 2024.*

* cited by examiner

INHALER AND METHOD

CROSS-REFERENCE TO RELATED APPLICATIONS

This application is a 371 filing from PCT/US2019/024902, filed Mar. 29, 2019, which claims the benefit of U.S. Provisional Patent Application, Ser. No. 62/650,464, filed Mar. 30, 2018.

FIELD OF THE INVENTION

The present invention generally relates to a device or apparatus useful for oral inhalation and delivery of a therapeutic agent or substance to the airways and lungs of a human subject. The invention includes a system and method for administering the therapeutic substance for treating an airway or pulmonary condition or soothing irritation of the airways or lungs.

BACKGROUND OF THE INVENTION

A variety of inhalation devices are currently known and available for administration and delivery of therapeutic substances to treat the airways and lungs of a human subject. Certain of these devices employ pressurized or mechanical means that must be coordinated with and initiated by the user to administer an aerosolized liquid or powder form of the therapeutic substance from a reservoir, such as a container or canister which holds and stores the therapeutic substance for use. These pressurized or mechanized delivery systems are referred to herein as "actuated inhalation devices" or "actuated inhalers."

Other devices depend solely upon the negative pressure of inhalation created by the user to deliver the therapeutic to the airways and lungs, referred to herein as "self-actuated inhalation devices" or "self-actuated inhalers."

For example, one of the most common type of assisted inhalation device delivers therapeutic substances in an aerosolized form or by virtue of an aerosol-type carrier or propellant that is compatible with the therapeutic substance. Such devices typically incorporate therapeutic substances contained under pressure within a canister or cartridge that attaches to or fits into the device. Once in place, the substance is released from the canister or cartridge by actuation initiated by the user that releases the therapeutic agent in aerosolized form. The aerosolized therapeutic agent or substance is then inhaled by virtue of the negative pressure of inhalation.

Many of these devices utilize replaceable the canisters or cartridges while other devices are disposable and typically include a built-in reservoir or chamber to house the therapeutic substance within the device. Once the reservoir is empty, the replaceable canister or disposable device is discarded.

Generally, actuated inhalers come in two configurations. The first type of actuated inhaler configurations requires the user to manually induce the release of the substance by physically pressing or pulling an actuator. The user must also coordinate his or her inhalation with such release in order to properly dispense the therapeutic agent into the airways and lungs.

The second type is of actuated inhaler configurations typically involves complex mechanisms to determine the proper time to release the substance once inhalation is initiated in order to maximize delivery of the substance into the user's airways and lungs (e.g. "breath-actuated" devices; see for example, U.S. Pat. No. 5,119,806 to Palson, et al.). These actuated inhaler devices are most often used to deliver therapeutics in aerosols or mist form, but they can also be used for delivering powderized solids.

Other known devices are specifically designed for delivering therapeutic substances solely by the negative pressure created by inhalation, i.e., they are "self-actuated." These devices are typically much simpler in design and less expensive to manufacture than inhalation assisted devices. Most often, these non-assisted devices are used to deliver therapeutics in a fine powder. One such device is commonly referred to as a turbo inhaler. These devices basically comprise an air intake, a powder reservoir and a mouthpiece. Upon inhalation initiated by the user, ambient air enters the device as an airstream and contacts the powdered therapeutic agent in the reservoir with enough force to carry the powder into the user's airways and lungs by virtue of airstream pressure.

Still other self-actuated inhalers utilize negative pressure created during inhalation to deliver a liquid therapeutic into the user's airways and lungs wherein the therapeutic substance or other liquid has been vaporized by heat or some other vaporization mechanism (see, for example, U.S. Pat. No. 8,833,364 to Buchberger).

Regardless of whether the device is fashioned to administer the therapeutic by actuated inhalation delivery or by self-actuated inhalation delivery, most of these devices are designed to deliver very precise metered doses which also adds to the complexity of construction as well as the manufacturing cost. For example, such devices typically have the therapeutic agent stored in a primary reservoir from which a precise quantity of the therapeutic must be transferred to a metered dose chamber prior to the user's inhalation of the substance. This precision calls for highly accurate manufacturing specifications and tolerances as well as strict quality control measures, both of which tend to increase complexity and cost for the device.

SUMMARY OF THE INVENTION

The present invention is directed to a self-actuated, oral inhalation device for the administration of a volatile therapeutic substance to the airways and lungs of a human subject for soothing irritation of the airways or lungs, wherein the volatile therapeutic agent is administered in vapor form. The term, "volatile therapeutic substance" means a substance or agent that does not require heat or propellant, pressure, or other external force or mechanism to vaporize the substance or agent, and excludes liquids or powders that require aerosolization for delivery. More particularly, the present invention is directed to a self-actuated inhaler capable of delivering a volatile therapeutic agent to the user's airways and lungs wherein the volatile therapeutic is contained in a replaceable dispensing cartridge or reservoir placed within the device during use.

The device of the present invention comprises a generally tubular body portion bounding a hollow inner chamber. The body portion comprises at a first end at least one or more air intake portals for the intake of ambient air into the chamber formed by the body portion, and at an opposing end, a mouthpiece configured so that the lips of the user can be positioned around the mouthpiece, generally forming an airtight seal around the mouthpiece to facilitate oral inhalation of vapor from the inhaler.

The body portion of the inhaler is preferably formed in an L-shape configuration when viewed from the side, where the intake portal or cartridge port is configured so the opening is along the vertical plane, and the mouthpiece is open along the horizontal plane when used. A preferred embodiment comprises an L-shape configuration having a body portion which is generally longer in dimension along the horizontal plane than the dimension of the vertically oriented body portion. The body portion can preferably comprise ergonomically formed indentations shaped to fit the hand or fingers to facilitate handling of the inhaler during use. The ergonomic formation can be, or can include, embossing or debossing in the body of the inhaler.

The body portion comprises a cartridge port for receiving a dispensing cartridge. The receiving port is oriented relative to the body portion to allow air entering the air intake(s) to pass by a cartridge placed within the cartridge port and transport volatile therapeutic agent downstream, toward and to the mouthpiece for delivery by oral inhalation to the user. The air intake port and cartridge port are preferably oriented in line with one another and are more preferably configured as one, port, e.g., the air intake port and the cartridge port are a single port.

In one embodiment of the invention, the device includes cover or cap for covering the air intake port or cartridge port. The cap for covering the cartridge port is preferably hingedly affixed to the body of the inhaler. In another embodiment of the invention, the device includes a mouthpiece cover for covering the mouthpiece when the device is not in use.

The subject invention further includes a cartridge which is configured to nest within the cartridge port of the inhaler during use. The cartridge is preferably formed in a generally elongate shape, having a substantially tubular and hollow body portion forming the side or side wall of the cartridge, and two ends. More preferably, the cartridge housing is provided in a shape and size which advantageously can deter use of the cartridge as a nasal inhaler. For example, in one preferred embodiment, the cartridge housing comprises a shape which is octagonal in cross-section. In a preferred embodiment, the cartridge housing is at least 1 cm, is at least 1.5 cm, is at least 2 cm, is at least 2.5 cm, or is at least 3 cm in diameter. In a preferred embodiment, the cartridge housing can include a ridged or threaded portion for matingly engaging a ridged or threaded portion on the inner face of the cartridge port. More preferably, the threads on the cartridge housing and cartridge port provide for engagement with less than two, and preferably about 1.5 turns.

The cartridge further comprises a wick portion disposed within the body portion of the cartridge. The wick portion, which can preferably be formed from an absorbent cloth or fiber material, can be saturated with a volatile therapeutic substance of choice and positioned within a cartridge housing.

The cartridge body comprises at least one escape portal, formed in the side wall or at least one end, for allowing the vapors of the volatile therapeutic agent to move into and fill the inhaler chamber with vapors of the therapeutic agent. The escape portal can be slot or slits formed into the body, or can be perforations or other apertures formed in the cartridge side wall or end.

Preferably, the cartridge body comprises a first open end which serves to receive the wick portion. The open end of the cartridge is preferably closed by a cartridge closing means, such as a cap or lid, when the wick portion is positioned therewithin, and is more preferably sealed to prevent direct contact of the wick portion by the user. The second end of the cartridge, can be open or closed, but is preferably permanently closed.

In one preferred embodiment, the cartridge is formed in a non-rounded geometric shape, i.e., non-circular or non-oval in cross-section, and is formed in a square, rectangular, pentagonal, hexagonal, or octagonal shape. This is advantageous so that he user does not confuse the cartridge with a nasal inhaler, or mis-use the cartridge as a nasal inhaler.

Accordingly, herein is provided various embodiments, features and advantages of the present invention that will be apparent to those of ordinary skill in the art in view of the following detailed description of the invention and accompanying drawings.

BRIEF DESCRIPTION OF THE DRAWINGS

The drawings as provided for herein set forth exemplary embodiments of the present invention, the detailed description of which follows hereinbelow. The drawings are merely exemplary and are clearly not intended to limit the invention as encompassed by the claims appended herewith.

In FIG. 4A, the mouthpiece is shown covered with mouthpiece cover 20; in FIG. 4B, the mouthpiece cover 20 is shown removed from mouthpiece 18, and showing the mouthpiece opening 21 through which the vapors of the volatile therapeutic agent or substance are inhaled by the user.

DETAILED DESCRIPTION OF THE INVENTION

The following description is made in general reference to FIGS. 1-4 and is provided herewith solely to illustrate exemplary embodiments of the present invention.

In accordance the present invention, there is described herein a self-actuated inhalation device for the oral administration of therapeutic substances to the airways and lungs of a human subject. Referring to the figures, preferred embodiments of the subject device are shown.

Figure 1:
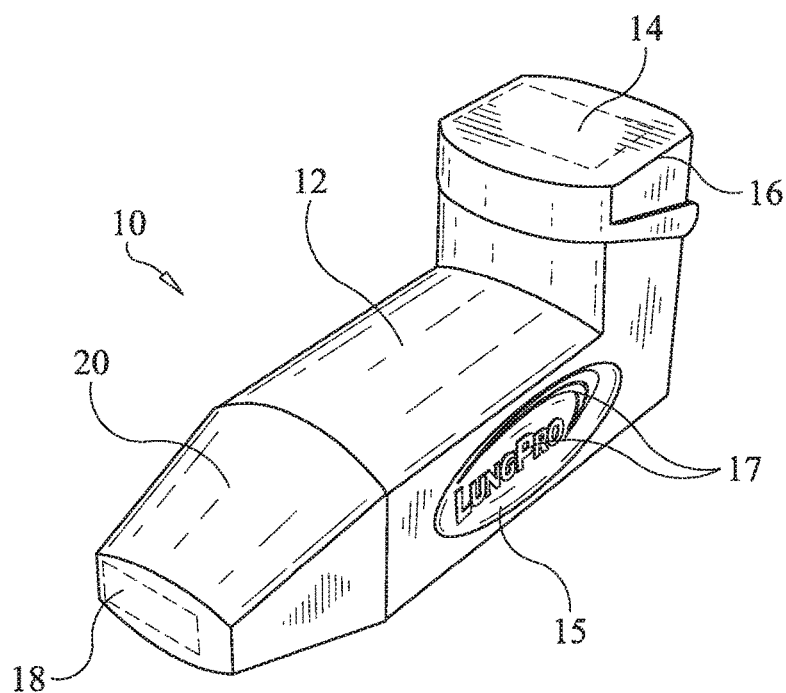
FIG. 1 is a perspective view of the inhaler of the present invention.

Turning to FIG. 1, the inhaler device of the present invention 10 comprises a generally tubular body portion 12 bounding a hollow inner chamber having at one end at least one or more air intake 14 (shown in phantom) for the intake of ambient air. The air intake can be covered by air intake cover 16. The inhaler device further comprises at the opposite end of the device, a mouthpiece 18 (shown in phantom) suitable for contacting the lips of a user in order to make an airtight seal during inhalation. The mouthpiece can be covered by a mouthpiece cover 20. Body portion 12 further comprises a cartridge receiving port 22 (not shown) for attaching and receiving a dispensing cartridge 24 as shown in FIG. 2.

Illustrated here is an indentation 15 formed in the side of the inhaler body for ergonomic facilitation of handling the device during use. Also illustrated are embossings 17 formed within the indentation to facilitate handling, preferably gripping, of the device during use. It would be understood that the indentation or embossing can be provided in a variety of shapes and configurations and are not limited to indentations, embossing, debossing or the like, and can be present or absent and, if present, can be in any combination or configuration so long as they facilitate gripping or handling of the device during use.

Figure 2:
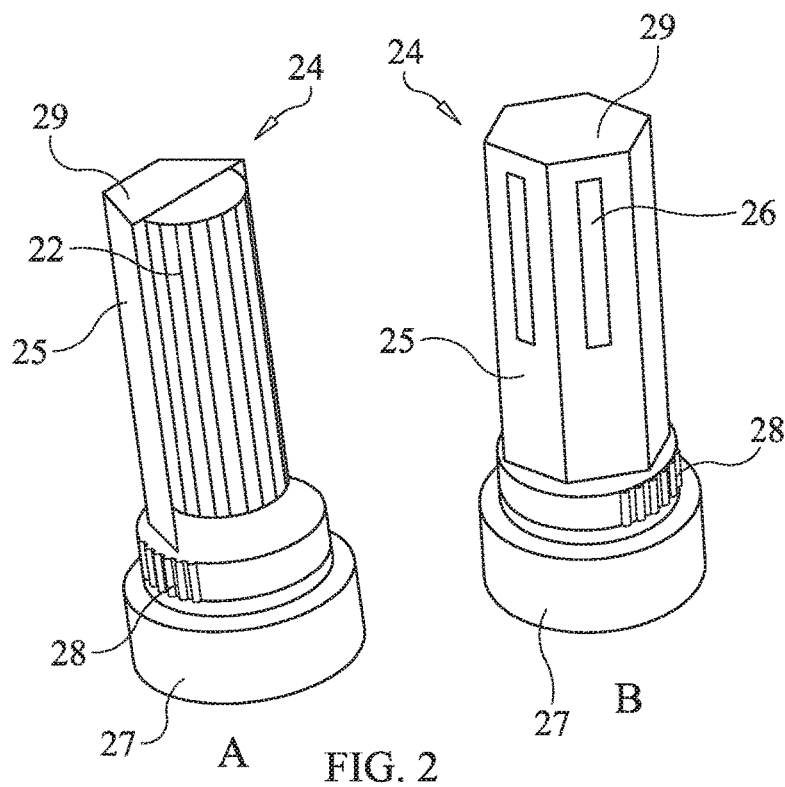
FIG. 2 is a perspective view of an exemplary cartridge for the inhaler of the present invention, shown in A as a cutaway view to illustrate the wick portion, preferably being an absorbent cloth or fiber material, disposed therewithin, and shown in B in full form to illustrate the escape portals formed as slots in the cartridge body.

FIG. 2 shows dispensing cartridge 24 to be used with the inhaler of the subject invention. FIG. 2A shows the cartridge housing or cartridge body portion 25 in cutaway view to illustrate the wick portion 22 disposed therein. The wick portion can be any absorbent synthetic or natural material or fabric that is compatible with a liquid, volatile therapeutic agent or substance and which allows for vaporization of the volatile therapeutic agent or substance therefrom. Such materials and fabrics are well known in the art and are commercially available.

FIG. 2B shows the cartridge housing or body portion in intact form, and illustrates the at least one escape portals 26 which allows the volatile therapeutic substance to vaporize or volatilize from the wick portion and into the inhaler body chamber when the device is being operated by a user.

Further illustrated in FIGS. 2A and 2B is the first end 27 of the cartridge body, shown here capped and sealed for containing the wick portion. A second end 29 of the cartridge body is shown in closed configuration.

The inhaler body and cartridge body are formed from a rigid, preferably lightweight material, and can be metal, plastic, or other suitable material capable of being formed in the configurations described. Preferably, the inhaler body and cartridge body are formed by injection-molded plastic or polymer material.

In a preferred embodiment, the cartridge housing provides a stepped cross-sectional shape comprising the elongate main body portion and the first end 27 having a larger diameter than the main body portion 25. This larger diameter can serve as a "stop" to prevent the cartridge from entering too far into the cartridge port and thereby becoming lodged and difficult to remove when being replaced. This larger diameter for the first end can also serve to facilitate the insertion and removal of the cartridge from the cartridge port by being easier to grasp and handle—the first end resting outside the cartridge port to facilitate removal by hand. One embodiment of the first end 27 of the cartridge provides a ridged or embossed outer surface to facilitate gripping the cartridge during insertion into or removal of the cartridge from the cartridge port.

Further, one embodiment can include a ridged or threaded portion 28 between the cartridge main body 25 and the first end 27. Preferably the diameter of the ridged or threaded portion 28 is an intermediate diameter, larger in diameter of the main body portion of the cartridge 25 and smaller in diameter than the diameter of the first end 27. In this embodiment, the ridged or threaded portion 28 can matingly engage with a complementary ridged or threaded portion provided on the inner surface of the cartridge port 14. These ridges or can advantageously serve to secure or lock the cartridge in place when in use.

Figure 3:
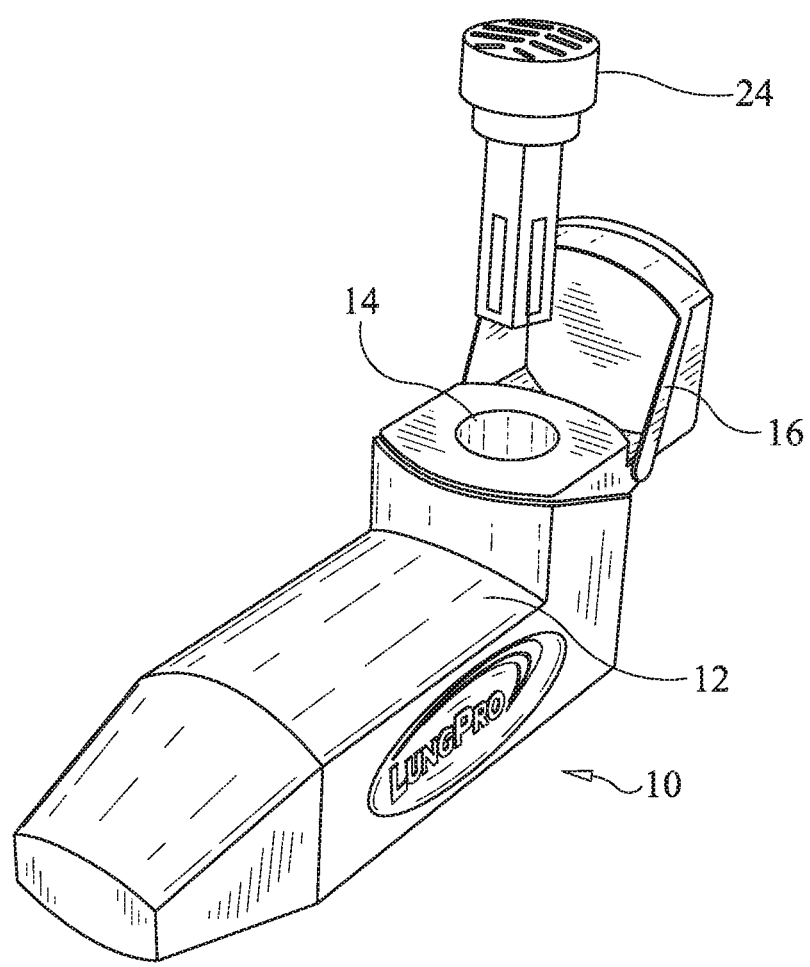
FIG. 3 is an exploded perspective view of the inhaler body and cartridge illustrating the positioning of the cartridge relative to the cartridge port, which is shown open or uncapped.

FIG. 3 shows an exploded view of inhaler 10 and cartridge 24 oriented in relation to one another when inserting or removing the cartridge from the cartridge port 14 of the inhaler body. The air intake port is shown here as the same element as cartridge port 14, but may be provided at a different position in the inhaler body. Air intake/cartridge port cap 16 is illustrated in open configuration, and hingedly affixed to inhaler body 12.

Figure 4:
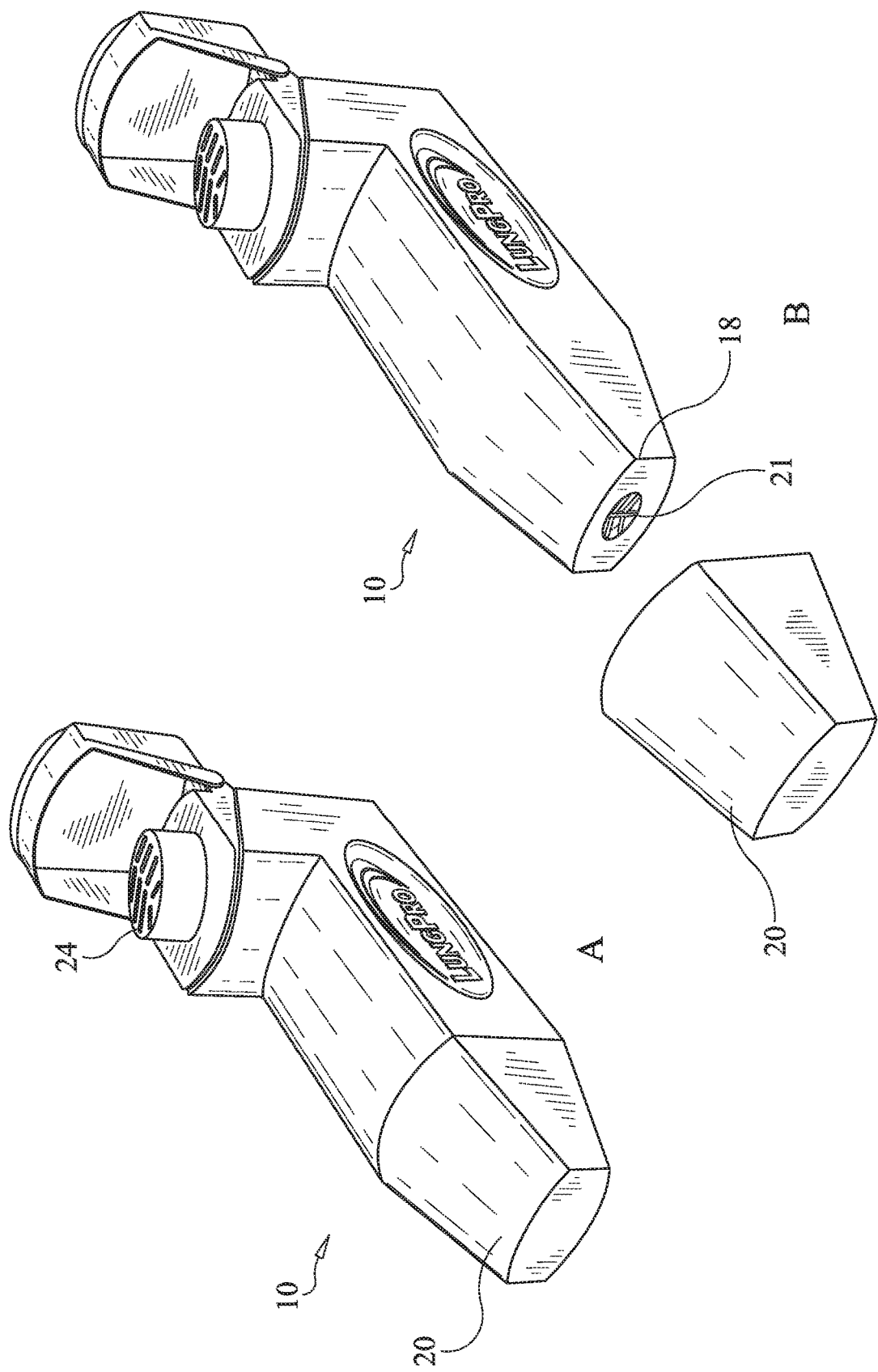
FIG. 4 is a perspective view of the inhaler of the subject invention, having the cartridge disposed within the cartridge port.

FIG. 4 shows perspective view of inhaler 10 and cartridge 24 oriented in relation to one another when the cartridge 24 (only one end of cartridge is visible) is inserted into the cartridge port and is positioned for use. Air intake cap 16 is illustrated in open configuration, and hingedly affixed to inhaler body 12. In FIG. 4A, the mouthpiece is shown covered with mouthpiece cover 20; in FIG. 4B, the mouthpiece cover 20 is shown removed from the exposed mouthpiece 18, and showing the mouthpiece opening 21 through which the vapors of the volatile therapeutic agent or substance are inhaled by the user. The opening may be an aperture or hold, or may be formed in different shapes or designs, an example of which is illustrated here.

It will be readily appreciated that receiving port 14 is situated relative to the internal aspect of the body portion such that when cartridge 24 is properly seated and attached to the body portion, air entering the air intake(s) may form an airstream adequate for the capture and transport of the volatile therapeutic agent by the airstream as it passes into and through the mouthpiece by negative pressure caused by inhalation. It will be further appreciated that the position and orientation of receiving port 22 must also be such that when cartridge 24 is properly seated and attached to body portion 12, escape portals 26 are adequately oriented with respect to the airstream to provide for adequate capture and transport of the volatile therapeutic during operation of the device.

In one embodiment of the invention, the device includes mouthpiece cover 20 for covering the mouthpiece when the device is not in use. The mouthpiece cover should be sufficient for maintaining a substantially airtight seal with the body portion to adequately preserve the therapeutic from unnecessary dissipation due to exposure to the ambient air. The mouthpiece cover may be fashioned from the same material as the body portion or from some other acceptable material so long as the material has suitable durability and can endure multiple attachments and removals over the life of the device.

In yet another preferred embodiment, the mouthpiece cover will be fashioned as a "snap cap" that can be snapped onto or into the mouthpiece to maintain an adequate seal. The snap cap can be fashioned for complete detachment or may be hinged or flexibly attached to the body portion as a flip cover using any of various means known by those skilled in the art such as hinges or flexible polymers. Alternatively, the cap may be fashioned as any one of several hundred plugs or screw caps well known in the art provided that the plug or cap makes a substantially airtight seal with the body portion to prevent the therapeutic from unnecessary dissipation into the ambient air when the device is not in use. It will be readily appreciated that in the event that a screw cap is employed, reciprocal threading must be located on the mouthpiece in order to secure the cap. The threading should preferably be located on the internal aspect of the mouthpiece for the comfort of the user. Such caps are commonly referred to as screw cap plugs and are readily known and available for incorporation into the device of the present invention.

In another embodiment of the invention, the device includes an air intake cover 16 for covering the air intake 14 when the device is not in use. The air intake cover should be sufficient for maintaining a substantially airtight seal with the body portion in sufficient proximity and configuration relative to the air intake so as to adequately preserve the therapeutic from unnecessary dissipation due to exposure to the ambient air.

Much like the mouthpiece cover, the air intake cover may be fashioned from the same material as the body portion or from some other acceptable material so long as the material has suitable durability and can endure multiple attachments and removals over the life of the device. In on preferred embodiment, the cover will be fashioned as a screw cap or a "snap cap" that can be snapped onto or into air intake to maintain an adequate seal. It can be fashioned for complete detachment or may be permanently attached to the housing as hingedly affixed to the body of the inhaler article, e.g., as a flip cover as mentioned above in the discussion of the mouth piece cover.

The cartridge comprises one or more escape portals 26 to allow a volatile therapeutic housed therein to escape from the internal aspect the cartridge where it is housed and to enter the airstream for capture and transport to and through the mouthpiece. In a further embodiment, the cartridge will comprise portal closure 29 for closing escape portal 26 when the device is not in use. The portal closure 29 should be sufficient for maintaining a substantially airtight seal with the cartridge housing 24 so that escape portal 26 is properly occluded in order to further preserve the therapeutic from unnecessary dissipation between uses. Optionally, the portal closures may be fitted with a safety seal that further ensures seal integrity between completion of manufacturing and user consumption, thereby promoting the shelf life of the therapeutic and ensuring that the contents remain unadulterated.

Cartridge 24 may be optionally fashioned to be replaceable or exchangeable allowing the user to use the device with various pre-formulated therapeutics dispensed within the cartridge. The open end of the cartridge may be closeable using a permanent seal or can be configured having a threaded cap which can threadedly engage the cartridge body, allowing access to the wick portion therewithin for replacing and disposing of the wick portion when the therapeutic agent is desired to be changed or replaced. The open end of the cartridge, whether sealed or capped, can also be configured to mate with the cartridge port formed in the inhaler body, whereby the cartridge can snap into the cartridge port, or can thread ably mate with the cartridge port.

Alternatively, the device can be fashioned as a disposable unit comprising the inhaler body and cartridge wherein the cartridge and inhaler body may be permanently affixed together during manufacture and used and discarded as a single unit or system.

While the inhaler of the present invention is adaptable for use with metered dose dependent, pharmaceutical grade inhalable therapeutics provided that a means for metered dose dispensing is incorporated into the design. Notwithstanding, the device is preferably utilized for non-metered dose dependent therapeutics that are self-volatilizing. Examples of these include natural or homeopathic therapeutics or cleansers designed to treat and cleanse the user's airways and lungs.

Accordingly, in one embodiment, the volatile therapeutic useful with the present invention comprises the infusion of the therapeutic while in the liquid phase into or on a medium having adequate porosity and retention characteristics suitable for retaining the liquid within it or on it, in sufficient quantities to render a vapor phase in equilibrium with the liquid phase such that the equilibrium constant is adequate for promoting the longevity of the product once the manufacturing seal has been broken.

Appropriate media for such infusion include various natural and synthetic wicking materials known and available in the arts of chemistry and material science. For example, the self-volatizing therapeutic or cleanser may be infused as a liquid into an absorbent medium such as a simple cotton wick which is placed into the cartridge and subsequently sealed during the manufacturing process to promote shelf life by preventing unnecessary dissipation of the therapeutic until use.

Although the design of the present invention is primarily intended for self-volatilizing therapeutics that do not require a vaporizing means, the device may be readily adapted for use with therapeutics or cleansers that require some assistance by a vaporization mechanism in order to adequately promote entry of the liquid into its vapor phase. Examples of these vaporization techniques and devices are well known to those skilled in the art and can be readily incorporated into the present invention in by those skilled in the mechanical design arts and manufacturing techniques.

Due to the inherent volatility of the preferred therapeutics and cleansers intended for administration using the present invention, it will be readily apparent to those skilled in the relevant arts that when designing the cartridge and the body portion, the cartridge should be received into or attached to the body portion in such fashion so as to orient the escape portals on the cartridge such that any escaping vapors are adequately directed into the airstream for capture and transport when the device is in the operative mode. Further, the cartridge must fit into or attach to the body portion in a such a manner to avoid leakage of the therapeutic from the escape portals into the ambient air.

In one of these embodiments, the cartridge is formed in a hexagonal canister shape that may be uniquely identifiable and distinguishable from the cartridges and canisters used in various pharmaceutical grade inhalation therapeutics.

A variety of materials for manufacturing inhalers are currently available and known in the art. Most commonly, inhalers such as disclosed by the present invention are fabricated from polymeric materials. Such polymers may include but are not limited to thermosetting polymers, thermoplastic polymers, and mixtures thereof. Moreover, it will be further apparent to those skilled in the art that selection of such polymers or copolymers should be such that the resulting polymeric matrix is of sufficient durability and rigidity.

In use, an inhaler body and cartridge of the subject invention, having the wick portion saturated with volatile therapeutic agent or substance, are provided to a user in need of the therapeutic agent or substance. If the inhaler body and cartridge are provided separately, the user opens the cartridge port cover, if present, and inserts the cartridge therein. The user can then place his or her lips to the uncapped mouthpiece when delivery of the therapeutic agent or substance is desired, and inhaling, by mouth, the vapors of the volatile therapeutic substance into the airways and lungs. Oral administration of the volatile therapeutic substance or agent can advantageously provide penetration of the vapors deep into the lungs.

The method of the invention concerns soothing or cleansing irritated airways or lungs using a volatile therapeutic agent or substance that is not a drug, as defined by the US Food and Drug Administration (FDA), but provides relief to airways and lining of the lungs of those that may be exposed to dust, soot or smoke in work or other environments. For example, employees such as wait staff or bartenders in bars or restaurants that allow smoking of cigarettes or cigars may become exposed to second-hand smoke during the course of working a shift in that bar or restaurant. These employees may desire to soothe the irritation caused by exposure to the smoke by using an inhaler and cartridge of the subject invention.

Persons exposed to smoke in work environments (e.g., factories or restaurants where open flames are used), soot (e.g., firefighters or fireplace maintenance workers) dust (housekeeping staff, or agricultural workers) or those that choose to smoke cigarettes or cigars, or have sensitivity to airway irritants, may also benefit by using the inhaler and cartridge of the subject invention. The result of using the inhaler and cartridge of the subject invention is a "cleansing" of the airways and lungs, whereby the user can refresh and reduce the irritated airways and lung lining.

While the invention has been described in its preferred forms or embodiments with some degree of particularity, it is understood that the detailed description as set forth herein has been provided only by way of example and that numerous modifications, changes, variations, substitutions and equivalents may be available as well as alternative details regarding construction, fabrication, and use, including the combination and arrangement of parts, all of the foregoing being readily apparent to those skilled in the art without departing from the spirit and scope of the present invention as described and claimed.

I claim:

1. A self-actuated inhaler providing vapors of a volatile liquid therapeutic agent to an airway or lungs of a user by mouth, said inhaler comprising:
   a housing forming a hollow body portion, said hollow body portion comprising:
     a first air intake portal for intake of ambient air into the inhaler body portion when actuated by negative pressure of inhalation by the user;
     a mouthpiece suitable for being contacted by mouth and lips of the user;
     a removable mouthpiece cover, the mouthpiece cover is configured to form a substantially airtight seal with the mouthpiece when the mouthpiece cover engages the mouthpiece;
     an air intake cover that is configured to move from an opened configuration to a closed configuration; and
     the first air intake portal forming a cartridge port being capable of receiving a dispensing cartridge containing the volatile liquid therapeutic agent, the dispensing cartridge comprising a top portion, an intermediate portion and a bottom portion, the top portion comprising a top wall and a side wall adjacent to the top wall and the intermediate portion, the bottom portion comprises a bottom wall and a side wall, the side wall of the bottom portion extending from the bottom wall to the intermediate portion, the top portion comprising a diameter that is larger than a diameter of the bottom portion, the top wall forming at least one inlet opening, the side wall of the bottom portion forming at least one outlet opening, the dispensing cartridge comprising a length that extends from the bottom wall to the top wall, the bottom wall and the side wall of the bottom portion formed a chamber for holding a wick having an absorbent material saturated with the volatile liquid therapeutic agent, the wick comprises a top surface, a bottom surface and a side surface extending from the top surface of the wick to the bottom surface of the wick, the wick is housed by the side wall of the bottom portion and the bottom wall of the bottom portion such that the at least one outlet opening and an interior surface of the side wall of the bottom portion is configured to face the side surface of the wick, the intermediate portion comprises at least one thread or at least one ridge formed on an outer surface of the intermediate portion, the least one thread or the at least one ridge of the cartridge is for engaging with the cartridge port to form a seal, wherein when the cartridge is received within the cartridge port and the air intake cover is in the opened configuration, the bottom portion and the intermediate portion are enclosed by the housing while a top surface of the top wall and a side surface of the side wall of the top portion are exposed to an outside of the inhaler and are not being covered by the housing, the air intake cover is configured to cover an entirety of the side and top surfaces of the top portion of the dispensing cartridge while the bottom portion and the intermediate portion the dispensing cartridge are received within the cartridge port, the air intake cover is configured to maintain substantially airtight seal with the housing in the closed configuration;
   wherein the mouthpiece and cartridge port are formed as a single unit and are situated relative to one another so that, under negative pressure of inhalation applied at the mouthpiece by the user, ambient air enters and flows through the at least one inlet opening of the dispensing cartridge, after the ambient air flows through the at least one inlet, the ambient air travels through the dispensing cartridge and through the at least one outlet of the dispensing cartridge before flowing through the mouthpiece, thereby delivering vapors of the liquid therapeutic agent into the airway or lungs of the user.

2. The inhaler of claim 1, wherein the dispensing cartridge has a non-rounded geometrical shape in cross-section.

3. The inhaler of claim 1, wherein the wick comprises a synthetic or natural material or fabric capable of allowing vaporization of the volatile liquid therapeutic agent.

4. The inhaler of claim 1, wherein the air intake portal cover is hingedly affixed to the body portion of the inhaler.

5. The inhaler of claim 1, wherein the cartridge and cartridge port engage to form an airtight seal.

6. The inhaler of claim 1, wherein the cartridge is detachably engaged with the cartridge port.

7. A method for soothing irritation of an airway or lungs of a user, said method comprising the steps of:
   a) providing the inhaler of claim 1,
   b) placing a user's lips onto the mouthpiece to form an airtight seal between the lips and the mouthpiece,
   c) applying negative pressure to the mouthpiece by the user inhaling, and
   d) inhaling into the airway or lungs of the user, the vapors of the volatile therapeutic agent from the dispensing cartridge.

8. The method of claim 7, wherein steps b), c), and d) are repeated as needed by the user.

9. The method of claim 7, wherein the dispensing cartridge is detachably engaged in the cartridge port, said method further comprising the steps of:
   e) replacing the dispensing cartridge with a second dispensing cartridge saturated with volatile liquid therapeutic agent and repeating steps b) through d) as needed.

* * * * *